United States Patent [19]

McCarthy

[11] Patent Number: 4,832,053

[45] Date of Patent: May 23, 1989

[54] UNIVERSAL TIE-LESS PATIENT TORSO RESTRAINT DEVICE

[76] Inventor: Andrew D. McCarthy, 5507 Albia Rd., Bethesda, Md. 20816

[21] Appl. No.: 178,977

[22] Filed: Apr. 7, 1988

[51] Int. Cl.$^4$ .............................................. A61F 13/00
[52] U.S. Cl. ..................................... 128/869; 128/874
[58] Field of Search ............... 128/134, 873, 874, 846, 128/875, 869; 2/69.5

[56] References Cited

U.S. PATENT DOCUMENTS

| | | |
|---|---|---|
| 1,573,446 | 2/1926 | Popham ............... 128/134 |
| 1,808,496 | 6/1931 | Dillon ................. 128/134 |
| 2,521,175 | 9/1950 | Kruse .................. 128/134 |
| 2,536,363 | 1/1951 | Godbout ............... 128/134 |
| 2,940,443 | 6/1960 | Baker .................. 128/134 |
| 3,136,581 | 6/1964 | Caballero ............. 128/134 |
| 3,407,807 | 10/1968 | Giberson ............. 128/134 |
| 3,788,309 | 1/1974 | Zeilman .............. 128/134 |
| 4,117,840 | 10/1978 | Rasure ................. 128/134 |
| 4,571,000 | 2/1986 | Holder ................. 128/134 |

FOREIGN PATENT DOCUMENTS 1350503 6/1964 France ..................... 128/134

Primary Examiner—Richard J. Johnson
Assistant Examiner—Michael Brown
Attorney, Agent, or Firm—Arthur R. Eglington

[57] ABSTRACT

A vest-like patient restraint garment presenting neck and arm apertures; the garment includes a unitary front and has at least two back panels each connected to the front panel. Each back panel has at least one elongated fastening strap secured at one of its longitudinal ends contiguous to the edge of each such panel.

The fastening straps extend toward and at least partially overlapping the remaining adjacent back panel.

One anchoring strap is provided for each fastening strap, with each such anchoring strap being adapted to cooperate with its respective fastening strap, with the length of the anchoring strap passing through the attachment means of the fastening strap.

Each of the anchoring straps terminate in mateable elements which form an anchor strap joinder and release means.

10 Claims, 2 Drawing Sheets

UNIVERSAL TIE-LESS PATIENT TORSO RESTRAINT DEVICE

This invention relates to a new device for restraining patients against unsafe (and spontaneous) movement by securing them to supports or fixtures. In one of its more specific aspects, the invention is concerned with a specially configured patient restraint device with multiple means for safely securing, and releasing, a patient to various supports.

A wide range of patients must be protected against unsafe and unhealthful movement - principally falling out of body supports such as bed, tables and chairs, or by moving body portions and thereby rupturing sutures, or otherwise causing further injury to already impaired body portions. Without being secured in such supports by health care personnel, such patients are likely to cause serious injury to themselves. Such patients include relative invalids, as well as those who have sufficient consciousness and strength to attempt to disengage such restraints, or engage in substantial movement, but who are also subject to sufficient aggression, disorientation or other debilitating condition, that disengaging their own restraints would likely result in injury to them. However, since the subject being restrained is a patient who is suffering from medical disability, such restraint must be comfortable and not overly confining in use to be acceptable.

Manually tied restraint devices are shown in the vests of U.S. Pat. Nos. #4,488,544 and 3,265,065, among others.

The act of strap tying is itself awkward and time-consuming for valuable health care personnel, particularly with an agitated patient.

Prior art tie-less restraint devices are bulky, complicated, awkward or restrictive in use, or they provide securing means which are accessible to the patient and thus susceptible to patient disengagement. Additionally, such devices pose special risks to patient safety.

Long-used restraint devices, are medically recognized as capable of serious mishap. Certain devices are described as dangerous; yet necessary evils in geriatric medicine; *Journal of Kentucky Medical Association*, August 1986, p. 397 et seq.; "Accidental Deaths in Aged Using Protective Devices." Recent reports in the *Journal of the American Medical Association* (JAMA), report several deaths caused by these vests in nursing homes, including cases of strangulation due to vest restraints and proposals that current vests be used more judiciously; JAMA, Nov. 21, 1986-Vol. 256, No. 19, p. 2725; and JAMA, Feb. 21, 1986-Vol. 255, No. 7, p. 905.

In sum, despite their long hisory of use and the variety of forms, serious mishaps do occur to agitated patients when currently available vest restraints are employed.

It is an object of the present invention to provide an improved torso restraint which is not subject to the above described limitations and hazards in use; and which is simple to secure and facile to release by the attending personnel. It is a further object of the invention to provide a garment which is readily formable into a vest and is tethered by a plurality of straps that are consistently secured and quickly releasable by the therapist.

It is a further object of the invention to provide a restraint vest wherein the tethering straps are individually adjustable to enable minimal patient shifting while restrained and thus preclude mattress sores. It is a further object of the invention to provide a restraining vest from which the patient can be removed more handily than is possible with currently used restraints, sometimes entailing separately tied knots for the strap anchoring.

Other objects and advantages of the present invention will become apparent from the following specification and from the drawings and the claims.

In accordance with the invention, a vest-like patient restraint is provided which comprises a unitary vest garment, preferably composed of a flexible material, and with neck and arm apertures, including a unitary front panel, and a pair of spaced-apart back panels with opposing edges, as shown in the accompanying drawings, in which.

The vertical edges are normally adapted not to overlap appreciably for reasons that will be made apparent. The vest body is cut so that its horizontal lower border, as it wraps around the patient torso, is positioned at just about waist level.

Each of the back panels has preferably at least two spaced apart vest fastening straps extending towards the opposing back panel with each such strap extending through an integral loop means and terminating at its free end in a rigid ring-like attaching means. Thus, there are four vest-securing (fastening) straps, in all, and a like number of anchoring ends.

Also provided to cooperate with each of the fastening straps, is an elongated anchoring strap, the body of which loops through a ring attaching means provided on the free end of the vest fastening straps. A vest with four securing straps will require four anchoring straps. Each anchoring strap is of a variable length, but is sufficient for it also to be looped around, preferably with a double-pass, the periphery of a stationary support post, which is conveniently a horizontal bar or railing on the bed itself, or it can be a distal stanchion pipe. The free ends of the anchoring strap terminate in mateable elements which form a single end attachment and release means, that closes the loop of the strap, while it is secured simultaneously to the fastener strap ring and the stationary post.

Figure 1:
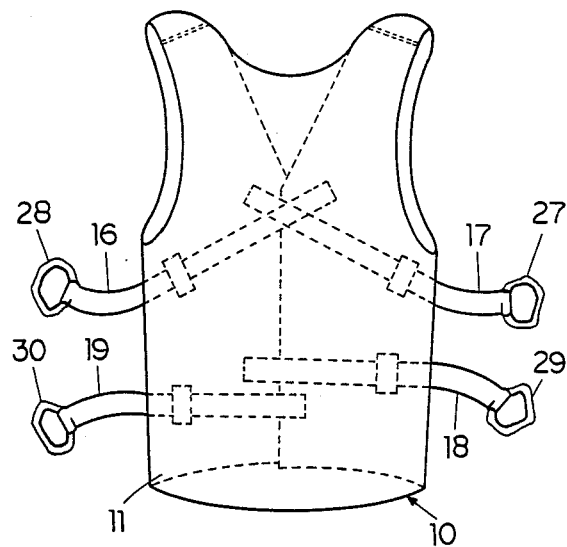
FIG. 1 is an elevational front panel view (chest-side) of the vest restraint of the present invention.
Figure 2:
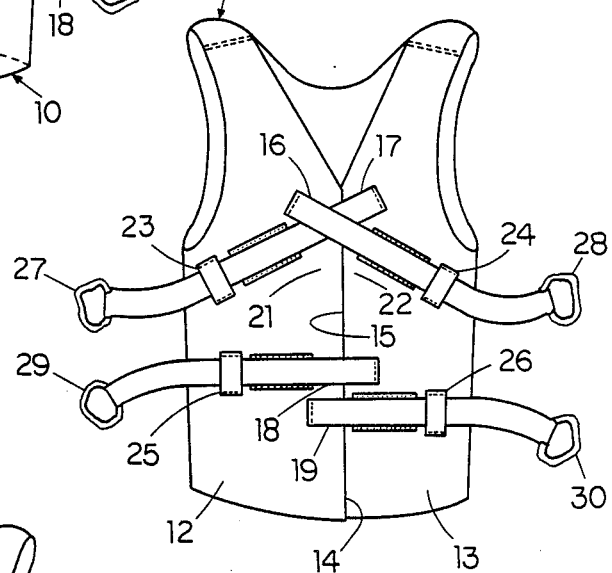
FIG. 2 is an elevational view of the reverse side of the vest garment of FIG. 1, showing the adjacent vest panels and their integral fastener straps.

As shown in the drawing, and in FIG. 1 in particular, the restraint vest, generally 10, of the present invention is fabricated of any suitable flexible material, such as a strong cloth, either of woven textile or vinyl coated fabric. It comprises an integral wrap-around-the-torso vest, having an integral front panel 11, which emerges rearwardly to form a pair of opposing left and right panels 12 and 13 (FIG. 2) having respective substantially vertical edges 14 and 15. In use, such vertically-oriented edges are spaced apart a varying distance, dependent upon the girth of the particular patient. Each of the reverse (back-side) panels 12 and 13, proximal to the vertical edges 14 and 15, have secured thereto a pair of spaced-apart, securing straps (four in all). Upper opposing pair 16 and 17 are secured at the one end to have a conveniently downwardly inclined orientation, when extended, and lower pair 18 and 19 are secured to be in a generally horizontally orientation, when extended. The straps maybe usefully oriented in other juxtapositions.

At the one end, the straps are each separately attached to the overlappable vest margins 21 and 22 of the back panel portions, as by edge-sewing, or the like. In the illustrated embodiment, each strap extends laterally from its respective supporting margin towards, and at least substantially overlaps the opposing back panel, normally passing through a suitable aligned flexible loop 23 to 26 composed of a reinforced fabric, or the like.

For example, upper strap 16, originating at and secured to the upper margin 21 of panel 12 extends and inclines across any vertical gap between the panel edges (not shown) over to adjacent panel 13, then through loop 24, leaving its free end available for lateral attachment.

The free ends of each of the fastener straps, 16–19, terminate in a preferably rigid loop fastener means, 27 to 30, such as a ring, either of metal or plastic. Each ring is retained by doubling back the strap free end, enclosing same over the ring bar portion, and conventionally secured as by sewing, or the like.

The fastener straps are of a preselected finite length, so that even with a torso of comparatively large girth, they are of a length such that the ring end, like 28, will at least extend through the loops 23 to 26, and extend beyond them at least an inch or more, so as to permit ring coupling to another of the component invention.

In FIG. 1, there is shown how the restraint vest of the present invention appears from the chest-side, (while worn by the patient - not seen) now being ready to be coupled with next to be described anchoring straps. The fastening straps, like 16, extend radially from the hidden portion of the vest to cooperate with anchoring straps which also connect stationary posts (see FIG. 6).

Figure 4:
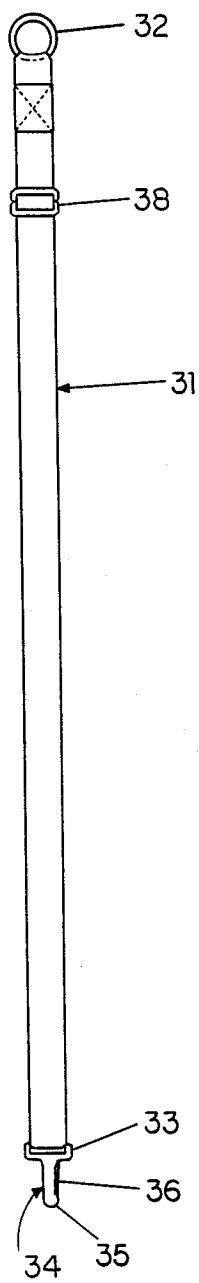
FIG. 4 is a plan view of the anchoring strap component of the invention, laid out flat before it is used to secure the fastener strap ends to remote stationary posts.

In FIG. 4, is a top plan view of the anchoring strap component 31, laid out in its full extension, as it would appear before its use in the present invention. At its one end, the anchor strap terminates in a rigid loop attachment means 32, such as a metal (or plastic) ring. This can be configured and secured, similarly to the rings 27–30 employed on the free end of the fastener straps 16 to 19.

The other end of anchor strap 31 is looped through a differently configured, rigid slot 33. Slot 33 is also integral with a simple and conventional snap fastener 34, typically one with a hook-shaped rigid end 35 and a cooperating flexible metal (or plastic) strip 36. Strip 36 is biased to be normally closed within the inner tip (not seen) of hooked end; it is adapted to be manually depressed so as to permit instant release of any ensnared bar or ring, like loop means 32.

Ring 32 of the anchor strap is the one with which the snappable joinder means 34 will cooperate, after the anchoring strap is properly looped through the fastener strap rings, like 27, for use with a vest. The free fabric end portion of anchor strap 31, which is located intermediate ring 32 and snap fastener 34 (not seen), is held by a conventional double-slot rigid buckle 38. The slidable buckle itself tracks left and right on the free length of the anchor strap 31 proper. In this manner, the overall length of anchor strap 31 is substantially variable, but is presettable so as to tightly straddle the distance between the vest attachment point (rings 27–30) and the particular stationary post(s), to be employed with the vest in use.

Figure 5:
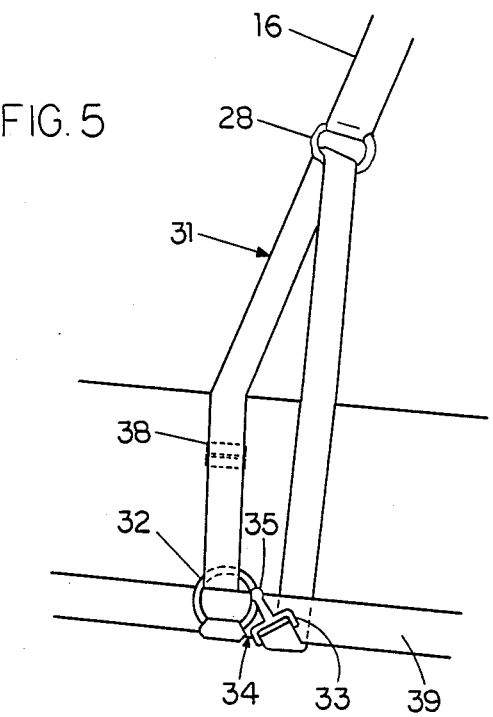
FIG. 5 is a fragmentary perspective view of one fastening strap cooperating with an anchoring strap of FIG. 4, which anchoring strap is, in turn, secured to a support post.

In FIG. 5 is a fragmentary view of the just described anchor strap component, now showing how one such adjustable-length anchor strap 31, and the complemental vest fastening strap 16, cooperate to secure the patient from excessive movement. It will be noted, as earlier described, that the anchor strap 31 has been threaded through the rigid ring 28 provided on fastener strap 16, and then is looped backwardly to permit joinder means 34 to close over the loop of ring 32. The anchor strap free ends are more conveniently linked adjacent to bed railing 39, which supports mattress 40.

It is important (for non-accessability by the restrained patient) where the anchoring strap is positioned and where its ends are joined relative to the cooperating fastening strap loop 28 and to an anchor point, like railing 39.

In the step of coupling with and limiting movement of the fastening straps, like 16, the rigid loop 32 of the anchor strap is first positioned adjacent the exterior surface of the horizontal length of the railing 39, as best shown in FIG. 5. Then, the clip fastener end 34 of the strap 31 is slipped through partly exposed loop 32, and both are cinched tight against railing 39. Then, end 34 is extended upwardly to pass (shown clockwise direction) through end ring 28 of the fastener strap 16. The free joinder end 34 is doubled backward toward the railing 39, so as to be linkable with loop 32. However, strap end 34 is first slipped under railing 39, before being snapped over rigid ring 32 via hook component 35.

This manner of linking with strap 16 negates any shifting of the anchor strap ring 32 during the course of erratic patient movement while he is in the restraint garment 10. The overall spread of the thusly closed anchor strap was, of course, preset by the use of sliding buckle 38.

Figure 6:
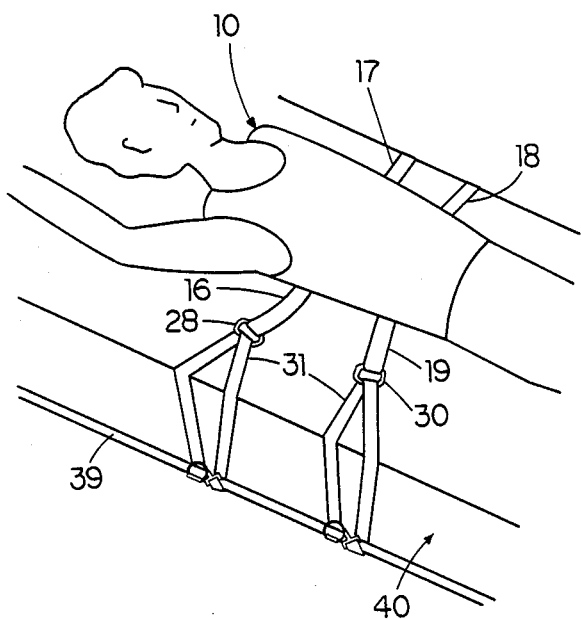
FIG. 6 is a perspective view of the vest restraint and plural cooperating straps in use with a resting patient.

In FIG. 6, it is seen how a patient, in wearing the present vest is safely restrained on a supporting bed 40, while still permitting him limited lateral, and lengthwise, torso movement. Such flexibility thus precludes the development of bed sores, and the like. It will be manifest that the restraint is employable with patients of varying girth, since the girth of the torso is quickly adjustable by manipulation of the securing straps and through the loops (24) and locking on the securing pads, to be described.

Figure 3:
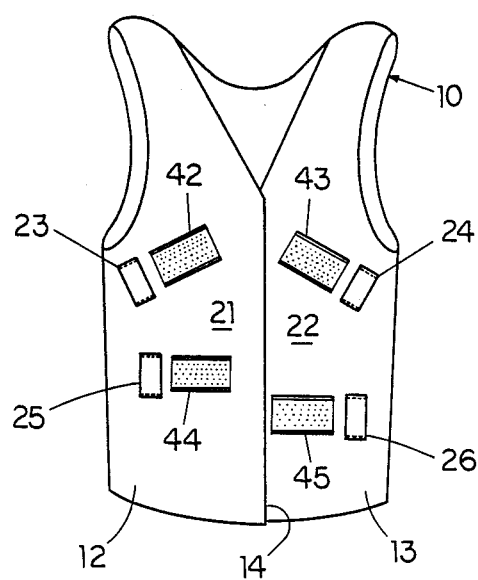
FIG. 3 is another elevational view of vest reverse side, omitting the fastener straps to reveal the optional supplemental locking pads for those fasteners.

In FIG. 3 is depicted another elevational view of the reverse side of the restraint, but with the fastener straps being omitted for clarity in seeing the supplemental strap securing means and strap guide loops. An upper pair of adhering pads 42 and 43 are affixed to vest panels 12 and 13 in spaced-apart (and an inclined orientation) to align with the fastener straps and their loops. A lower pair of like-length adhering pads on strap fasteners 44 and 45, are positioned directly and spacedly below the upper pair, but these are in a substantially horizontal orientation. The pads cooperate with complementary segments on the inward faces (not seen) of the securing straps 16 to 19 and the flexible loops 23 to 26, as best shown in FIG. 3.

This added securing feature for the strap body, like 16, serves to provide a safe and comfortable fit for the restraint, which is independent of the movement-limiting functioning of the cooperating anchoring strap, like 31. Such Velcro-type ancillary fastening means on the vest back panels will also reduce the risks already seen with loosely fitting restraint vests, and from too loose vests slipping into a ligature mode and possibly obstructing patient ventilation, as has been reported in the medical literature discussed earlier.

Conveniently, the opposing pads 42 to 45 are of the well known Velcro adhesive pile and hook-locking means, that is manually compressed after the straps are in place. The adhered pads can be handily separated when the vest is to be removed, by manually pulling apart the Velcro locking means, and retracting the fastener strap end rings 27 to 30 through loops 23 to 24, respectively. The restraint 10 is quickly removed from the patient, as needed.

As for the juxtapositions of the Velcro fastener means components, the adhesive pile component may be more conveniently mounted on the vest panels and the tiny hooks pad mounted on undersides of the fastener straps. Either arrangement is operable.

The restraining vest of the present invention provides a marked improvement over earlier known garments. It provides for secure restraining, which cannot be released by the restless patient, since the sliding buckle 38 and the snappable fastener 36 on strap 31, are located distally from him; yet, it is comparatively inexpensive to fabricate, requiring no unusual hardware. It also involves no component which can become hazardous to the patient.

Most impressively, it handily permits necessary re-adjustments of the patient's body, without risking an injurious fall from the supporting bed, or any contortions by agitated patient that could convert the vest edges into a strangulation ligature, as has been discussed.

I claim:

1. A patient restraint, comprising:

a vest-like garment presenting neck and arm apertures, such garment including a unitary front comprising a front panel.

At least two back panels each connected to the front panel, each of the said back panels having a substantially vertically-oriented edge, and each such back panel having at least one elongated fastening strap secured at one of its longitudinal ends contiguous to such vertically-oriented edge of each such panel; a second elongated fastening strap secured at one longitudinal end along said edge of each back panel and being spaced apart from and appreciably above the first opposing pair of fastening straps, the free end of each of said fastening straps extending toward and at least partially overlapping the remaining adjacent back panel, each such strap free end extending through a loop means secured to said adjacent back panel;

each of said fastening straps terminating at its free end in an attachment means: an one anchoring strap for each fastening strap, each such anchoring strap being adapted to cooperate with its respective fastening strap, with the length of the anchoring strap passing through said attachment means of the fastening strap;

each of said anchoring straps terminating in mateable elements which form an anchor strap joinder and release means, each of said anchoring straps being of a length sufficient for it to be looped around a support post which is spaced apart from the garment so as not to be readily accessible to a restrained patient, and each strap includes means for adjusting the overall length of said anchoring strap.

2. The restraint of claim 1 in which the means for adjusting the overall length of said anchoring strap comprises a slideable buckle means to which one terminus of the strap material is secured and which buckle means has integral slots which track on the intermediate portion of the length of the anchor strap with its particular location defining the variable overall strap length.

3. The restraint of claim 2 in which the variable length adjustable anchoring strap further comprises having one free end of the strap extending and passing its elongate free length through a loop like attachment means affixed at the free end of the fastener strap and also forming one of the said mateable joinder and release elements, said elongate free length of the strap material extending oppositely towards and passing through the integral slots of the said slideable buckle means, with the other strap free end terminating in secure attachment to the other of said mateable attachment elements.

4. The restraint of claim 1 in which said strap joinder and release means are adapted to be positioned proximal to said support post and relatively remote from the patient.

5. The restraint of claim 1 comprising at least four attached anchoring straps with each connecting at one point along its length with one of at least four vest-mounted fastening straps and further adapted for securing each of said anchoring straps at another point along its length to different anchor post locations sufficiently spaced apart for restraining the patient torso from lateral and longitudinal movement that could be hazardous.

6. The restraint of claim 5 wherein said different locations are stationary post supports.

7. The restraint of claim 1 in which intermediate portions of the surface of said fastening straps that overlay said back panels, and the underlying back panel portions contain cooperating hook and adhesive pad securing materials on the directly opposing surfaces thereof.

8. The restraint of claim 7 in which the pad securing materials have the adhesive pile component on the back panels and the cooperating hooks pad component disposed on the undersurface of the fastener straps.

9. The restraint of claim 1 in which the mateable elements of said anchor strap joinder and release means comprise a ring-like means at one free end and a manually-activated hooking means at the other free end.

10. The restraint of claim 1 in which the second and upper pair of opposing fastening straps have a downwardly inclined orientation placing the free ends of said straps in a spaced apart alignment that is closer than their other longitudinal ends which are secured to said back panels.

* * * * *